United States Patent [19]

Föry

[11] Patent Number: 4,603,211

[45] Date of Patent: * Jul. 29, 1986

[54] PROCESS FOR THE PREPARATION OF 1,2-BENZOXATHIINE DERIVATIVES

[75] Inventor: Werner Föry, Basel, Switzerland

[73] Assignee: Ciba-Geigy Corporation, Ardsley, N.Y.

[*] Notice: The portion of the term of this patent subsequent to Dec. 24, 2002 has been disclaimed.

[21] Appl. No.: 656,193

[22] Filed: Oct. 1, 1984

[51] Int. Cl.$^4$ .................. C07D 327/06; C07D 307/28
[52] U.S. Cl. ..................... 549/15; 549/467; 544/212; 544/297
[58] Field of Search ............... 549/15, 467; 544/212, 544/297

[56] References Cited

PUBLICATIONS

Clancy et al, C.A., vol. 79, 1973, 79:105159t.

Primary Examiner—Henry R. Jiles
Assistant Examiner—J. G. Mullins
Attorney, Agent, or Firm—Karl F. Jorda

[57] ABSTRACT

A novel process for the preparation of 3,4-dihydro-2,2-dioxo-3-methyl-1,2-benzoxathiin-8-ylsulfonamide of the formula I

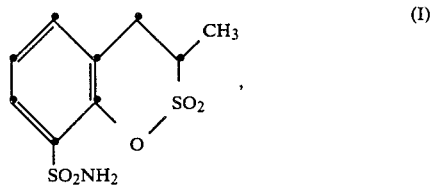

(I)

reacting a 5-halo-2,3-dihydro-2-methylbenzo[b]furan of the formula II

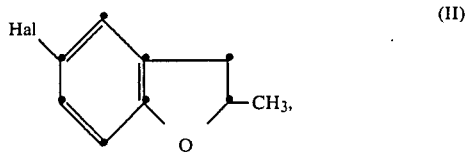

(II)

wherein Hal is chlorine or bromine, with chlorosulfonic acid to give a 6-halo-2,2-dioxo-3-methyl-1,2-benzoxathiin-8-ylsulfonyl chloride of formula III

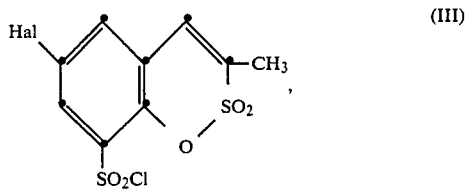

(III)

wherein Hal is chlorine or bromine, converting this sulfonyl chloride with ammonia into a 6-halo-2,2-dioxo-3-methyl-1,2-benzoxathiin-8-ylsulfonamide of formula IV

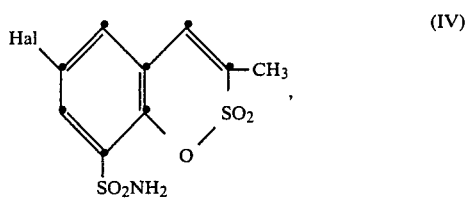

(IV)

wherein Hal is chlorine or bromine, dehalogenating this sulfonamide with hydrogen in the presence of a tertiary amine and a noble metal catalyst, and hydrogenating the resultant 2,2-dioxo-3-methyl-1,2-benzoxathiin-8-ylsulfonamide of formula V

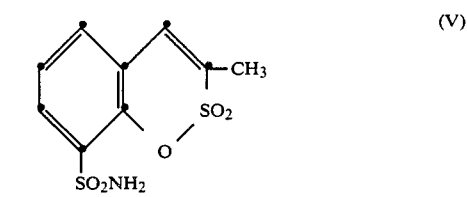

(V)

with hydrogen in the presence of a noble metal catalyst.

11 Claims, No Drawings

PROCESS FOR THE PREPARATION OF 1,2-BENZOXATHIINE DERIVATIVES

The present invention relates to a novel process for the preparation of 3,4-dihydro-2,2-dioxo-3-methyl-1,2-benzoxathiin-8-ylsulfonamide.

The 3,4-dihydro-2,2-dioxo-3-methyl-1,2-benzoxathiin-8-ylsulfonamide obtainable by the process of this invention is a valuable intermediate for the preparation of herbicides and plant growth regulators of the class of the sulfonylureas. Such compounds and their biological properties are known for example from published European patent application EP-A-99 339.

The preparation of compounds having the 1,2-benzoxathiine structure has been described in various publications: Int. J. Sulfur Chem., A, Volume 2, No. 4, 249–255 (1972) or EP-A-107 979. The procedures employed are poorly suited to large-scale production, as they proceed via a relatively large number of process steps.

Accordingly, there is a need for a simple synthesis comprising a few reaction steps and permitting the production of the desired intermediate in good yield.

Surprisingly, it has now been found that it is possible to prepare 3,4-dihydro-2,2-dioxo-3-methyl-1,2-benzoxathiin-8-ylsulfonamide of the formula I

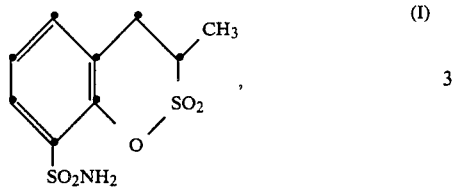

by reacting a 5-halo-2,3-dihydro-2-methylbenzo[b]furan of the formula II

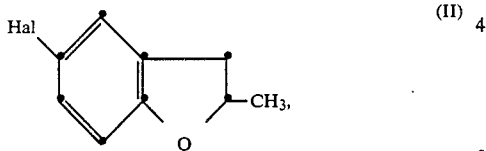

wherein Hal is chlorine, bromine or iodine, with chlorosulfonic acid to give a 6-halo-2,2-dioxo-3-methyl-1,2-benzoxathiin-8-ylsulfonyl chloride of formula III

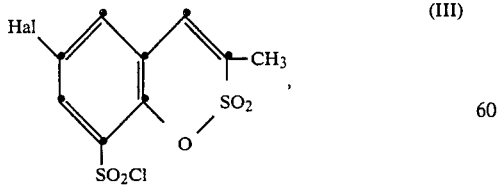

wherein Hal is chlorine, bromine or iodine, converting this sulfonyl chloride with ammonia into a 6-halo-2,2-dioxo-3-methyl-1,2-benzoxathiin-8-ylsulfonamide of formula IV

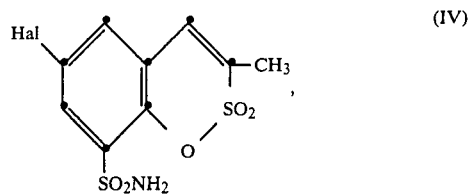

wherein Hal is chlorine, bromine or iodine, dehalogenating this sulfonamide with hydrogen in the presence of a tertiary amine and a noble metal catalyst, and hydrogenating the resultant 2,2-dioxo-3-methyl-1,2-benzoxathiin-8-ylsulfonamide of formula V

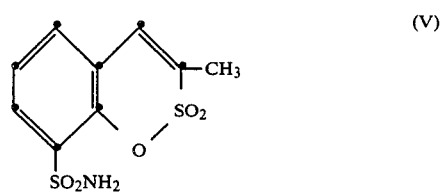

with hydrogen in the presence of a noble metal catalyst.

Within the scope of this invention, Hal denotes chlorine, bromine or iodine, with chlorine and bromine being preferred.

The reaction product of formula I can be reacted, in known manner, direct or in the form of the corresponding isocyanate or of a carbamate to give a herbicide of the class of the sulfonylureas.

The starting compound of formula II is known and can be prepared by halogenating 2,3-dihydro-2-methyl-benzo[b]furan.

Commercially available chlorosulfonic acid is employed for carrying out the first step (II→III) of the process of this invention. At least 3 moles of chlorosulfonic acid are used per mole of compound of formula II. It is convenient to use a substantial excess, for example at least 5 moles, of chlorosulfonic acid per mole of compound II. In individual embodiments of the process, the chlorosulfonic acid can be used simultaneously as reactant and as solvent. In general, however, the reaction (II→III) is carried out in an inert solvent. Suitable solvents are carbon disulfide, ethyl acetate, and chlorinated hydrocarbons such as methylene chloride, chloroform, carbon tetrachloride, 1,2-dichloroethane, 1,2-dichloroethylene, tetrachloroethylene, chlorobenzene or dichlorobenzene. The preferred solvents are methylene chloride, 1,2-dichloroethane and chloroform. The reaction temperatures are normally in the range from −10° to +80° C., preferably from −10° to +60° C.

In a preferred embodiment of the first reaction step (II→III), the compounds of formula III, wherein Hal is chlorine or bromine, are prepared by reacting an appropriate compound of formula II with at least 3 moles of chlorosulfonic acid per mole of compound of formula II, in an inert solvent and in the temperature range from −10° to +80° C. The most preferred embodiment of the process of the invention is that in which the reaction (II→III) is carried out in the temperature range from −10° to +60° C. in methylene chloride, 1,2-dichloroethane or chloroform, with at least 5 moles of chlorosulfonic acid per mole of compound of formula II.

The conversion of the sulfonyl chloride of formula III into the corresponding sulfonamide of formula IV is carried out under the conditions customarily employed for this per se known reaction step, for example by treating the compound of formula III with an aqueous solution of ammonia under normal pressure and at room temperature, or by treating a compound of formula III with ammonia in an inert solvent and optionally in the presence of an acid acceptor. Examples of suitable solvents and acid acceptors are: carbonates such as sodium and potassium carbonate, bicarbonates such as sodium and potassium bicarbonate, oxides such as calcium and magnesium oxide, or hydroxides such as sodium, potassium, calcium or magnesium hydroxide; ethers such as diethyl ether, tetrahydrofuran, dioxan, ethylene glycol dimethyl ether or diethylene glycol dimethyl ether; or hydrocarbons such as cyclohexane, benzene, toluene or xylene. The reaction with an aqueous solution of ammonia is preferred.

The dehalogenation of the compound IV to give the compound V by catalytic hydrogenation is generally carried out under mild conditions at room temperature under normal pressure, with hydrogen, in an inert solvent and in the presence of an acid acceptor. The catalysts employed are generally noble metal catalysts such as platinum or palladium in the form of platinum oxide, platinum black, platinum on barium sulfate, palladium black or palladium on carbon. The most widely used catalyst is palladium on carbon in commercial form as 5% palladium/carbon.

The acid acceptors ordinarily employed are: carbonates such as sodium, potassium or calcium carbonate, bicarbonates such as sodium or potassium bicarbonate, oxides such as magnesium or calcium oxide, and, preferably, tertiary organic amines such as trimethylamine, triethylamine, diazabicyclo[2.2.2]octane, 1,8-diazabicyclo[5.4.0]undec-7-ene, 1,5-diazabicyclo[4.3.0]non-5-ene, pyridine, quinoline or isoquinoline. Suitable solvents are: ethers such as diethyl ether, tetrahydrofuran or dioxan; esters such as ethyl acetate; alcohols such as methanol, ethanol, n-propanol or 1-propanol; and hydrocarbons such as pentane, hexane, cyclohexane, benzene, toluene or xylene. In the preferred embodiment of the process, the compound of formula IV is hydrogenated in tetrahydrofuran with hydrogen, under normal pressure at 20° to 25° C., in the presence of a 5% palladium on carbon catalyst.

The catalytic hydrogenation of the non-aromatic double bond of the compound V in the final reaction step (V→I) is carried out under more severe conditions as compared with the previous reaction step (IV→V), i.e. both the pressure of the hydrogen atmosphere and the temperature are advantageously increased. Preferred conditions are a pressure from 1 to 10 bar and a temperature range from 30° to 60° C. The catalyst and the solvent are selected from the same groups as those employed in the previous reaction step. In the preferred embodiment of the process, the compound V is hydrogenated in tetrahydrofuran at 30° to 60° C. under a pressure of 1 to 5 bar and in the presence of a 5% palladium on carbon catalyst.

A preferred embodiment of the process of this invention for the preparation of compounds of formula I comprises reacting a compound of formula II, wherein Hal is bromine or chlorine, with at least 5 moles of chlorosulfonic acid per mole of compound of formula II in the temperature range from −10° to +60° C., in methylene chloride, 1,2-dichloroethane or chloroform, treating the resultant sulfonyl chloride of formula III with an aqueous solution of ammonia, dehalogenating the sulfonamide of formula IV so obtained by catalytic hydrogenation in tetrahydrofuran with hydrogen, under normal pressure in the temperature range from 20° to 25° C. and in the presence of a 5% palladium on carbon catalyst, and hydrogenating the dehalogenated sulfonamide of formula V in the temperature range from 30° to 50° C. under a pressure of 1 to 5 bar in the presence of a 5% palladium on carbon catalyst.

The invention is illustrated in more detail by the following Examples. Example P3 will be understood as representing a variation of the second reaction step of Example P1.

PREPARATORY EXAMPLES

EXAMPLE P1:

3,4-Dihydro-2,2-dioxo-3-methyl-1,2-benzoxathiin-8-ylsulfonamide (a) 5-Bromo-2,3-dihydro-2-methylbenzo[b]furan A solution of 215 ml of bromine in 450 ml of methylene chloride is added dropwise over 2½ hours to an ice-cooled mixture of 562.3 g of 2,3-dihydro-2-methylbenzo[b]furan, 1600 ml of methylene chloride, 1600 ml of water and 352.5 g of sodium bicarbonate. After the mixture has been stirred for another 1½ hours at the same temperature, the aqueous phase is separated and extracted with two 300 ml portions of methylene chloride. The combined organic phases are washed with 2×250 ml of water, dried over sodium sulfate and concentrated. After removal of all constituents having a boiling point below 99° C. under a pressure of 8 mbar, there are obtained 750.7 g of 5-bromo-2,3-dihydro-2-methylbenzo[b]furan as residue.

(b) 6-Bromo-2,2-dioxo-3-methyl-1,3-benzoxathiin-8-ylsulfonylchloride 400 ml of chlorosulfonic acid are added dropwise over 20 minutes to a solution of 160 g of 5-bromo-2,3-dihydro-2-methylbenzo[b]furan in 460 ml of absolute chloroform, which solution has been cooled to −7° C. The mixture is stirred at a temperature of 15° C. for 15 minutes and then stirred dropwise over 35 minutes into a mixture of 1.5 kg of ice, 1000 ml of water and 500 ml of chloroform. After this mixture has been stirred for 15 minutes at 0° C., the organic phase is separated and the aqueous phase is extracted with 3×250 ml of chloroform. The combined organic extracts are washed with 150 ml of water, dried over sodium sulfate and concentrated, affording 180 g of 6-bromo-2,2-dioxo-3-methyl-1,2-benzoxathiin-8-ylsulfonyl chloride as oily residue which can be further processed direct.

(c) 6-Bromo-2,2-dioxo-3-methyl-1,2-benzoxathiin-8-ylsulfonamide

A solution of 180 g of 6-bromo-2,2-dioxo-3-methyl-1,2-benzoxathiin-8-ylsulfonyl chloride in 500 ml of tetrahydrofuran is added dropwise over 30 minutes to 307 ml of a 30% aqueous solution of ammonia. The mixture is stirred for 30 minutes at 20° C. and concentrated under reduced pressure at 45° C. The residue is triturated with 200 ml of ether. The precipitate is isolated, washed with water and dried at 45° C., affording 63.2 g of 6-bromo-2,2-dioxo-3-methyl-1,2-benzoxathiin-8-ylsulfonamide of m.p. 243°–245° C. (crystallisation from ethanol).

(d) 2,2-Dioxo-3-methyl-1,2-benzoxathiin-8-ylsulfonamide 120 g of 6-bromo-2,2-dioxo-3-methyl-1,2-benzoxathiin-8-ylsulfonamide are dissolved in 2.4 liters of tetrahydrofuran and the solution is hydrogenated with hydrogen for 40 minutes, in the presence of 41.3 g of triethylamine and 12.0 g of 5% palladium on carbon catalyst, under normal pressure and in the temperature range from 20° to 25° C. The mixture is filtered, the filtrate is concentrated, and the residue is taken up in 1300 ml of hot 90% aqueous ethanol. The insoluble constituents are separated and the solution is cooled to 0° C. The precipitate is separated and dried, affording 70 g of 2,2-dioxo-3-methyl-1,2-benzoxathiin-8-ylsulfonamide of m.p. 204°–205° C.

(e) 10.0 g of 2,2-dioxo-4-methyl-1,2-benzoxathiin-8-ylsulfonamide are dissolved in 200 ml of tetrahydrofuran and the solution is hydrogenated with hydrogen for 2½ hours, in the presence of 2.0 g of 5% palladium on carbon catalyst, under a pressure of 4 bar and at a temperature of 40° C. After removal of the catalyst the solution is concentrated and the residue is crystallised from 120 ml of 70% aqueous ethanol, affording 9.0 g of 3,4-dihydro-2,2-dioxo-3-methyl-1,2-benzoxathiin-8-ylsulfonamide of m.p. 185°–186° C.

EXAMPLE P2:

N-(3,4-Dihydro-2,2-dioxo-3-methyl-1,2-benzoxathiin-8-ylsulfonyl)-N'-(4-methoxy-6-methylpyrimidin-2-yl)urea A mixture of 3.33 g of 3,4-dihydro-2,2-dioxo-3-methyl-1,2-benzoxathiin-8-ylsulfonamide, 1.84 ml of 1,8-diazabicyclo[5.4.0]undec-7-ene, 3.2 g of N-(4-methoxy-6-methylpyrimidin-2-yl)phenylcarbamate and 35 ml of absolute dioxan is stirred for 45 minutes at a temperature in the range from 20° to 25° C. The mixture is concentrated and the oily residue is triturated with ether and 14 ml of 1N hydrochloric acid. The crystalline precipitate obtained is isolated, washed with water and dried, affording 4.96 g of N-(3,4-dihydro-2,2-dioxo-3-methyl-1,2-benzoxathiin-8-ylsulfonyl)-N'-(4-methoxy-6-methylpyrimidin-2-yl)urea of m.p. 215°–218° C.

EXAMPLE P3:

6-Bromo-2,2-dioxo-3-methyl-1,2-benzoxathiin-8-ylsulfonyl chloride 133 ml of chlorosulfonic acid are added dropwise at a temperature from 40° to 50° C. over 30 minutes to a solution of 42.6 g of 5-bromo-2,3-dihydro-2-methylbenzo[b]furan in 120 ml of chloroform. The mixture is heated to reflux for 4 hours and, after being cooled to 0° C., added dropwise over 30 minutes to a mixture of 400 g of ice, 500 ml of water and 100 ml of chloroform. The organic phase is separated and the aqueous phase is extracted with 3×100 ml of chloroform. The combined organic phases are washed with water and concentrated, affording 72.2 g of 6-bromo-2,2-dioxo-3-methyl-1,2-benzoxathiin-8-ylsulfonyl chloride as oily residue.

What is claimed is:

1. A process for the preparation of 3,4-dihydro-2,2-dioxo-3-methyl-1,2-benzoxathiin-8-ylsulfonamide of formula I

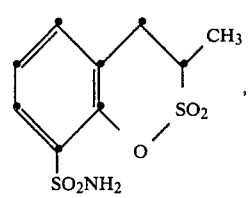

(I)

which comprises reacting a 5-halo-2,3-dihydro-2-methylbenzo[b]furan of the formula II

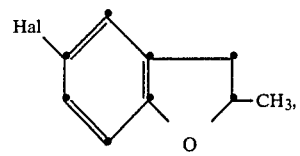

(II)

wherein Hal is chlorine or bromine, with chlorosulfonic acid to give a 6-halo-2,2-dioxo-3-methyl-1,2-benzoxathiin-8-ylsulfonyl chloride of formula III

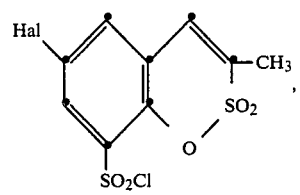

(III)

wherein Hal is chlorine or bromine, converting the sulfonyl chloride with ammonia into a 6-halo-2,2-dioxo-3-methyl-1,2-benzoxathiin-8-yl-sulfonamide of formula IV

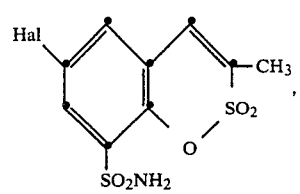

(IV)

wherein Hal is chlorine or bromine, dehalogenating this sulfonamide with hydrogen in the presence of a tertiary amine and a noble metal catalyst, and hydrogenating the resultant 2,2-dioxo-3-methyl-1,2-benzoxathiin-8-ylsulfonamide of formula V

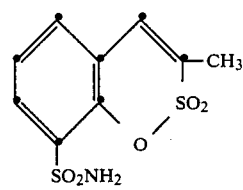

(V)

with hydrogen in the presence of a noble metal catalyst.

2. A process according to claim 1, wherein Hal is chlorine or bromine.

3. A process according to claim 1, wherein the reaction is carried out in all steps in the temperature range from −10° to +80° C., preferably from −10° to +60° C.

4. A process according to claim 1, wherein the individual reaction steps are carried out in inert solvents.

5. A process according to claim 4, which comprises carrying out the reaction of the compound of formula II to give the compound of formula III in methylene chloride, 1,2-dichloroethane or chloroform, the reaction of the compound of formula III to give the compound of formula IV in water, and the reactions of the compound of formula IV to give the compound of formula V and of the compound of formula V to give the compound of formula I in tetrahydrofuran.

6. A process according to claim 1, wherein the reaction of the compound of formula II to give the compound of formula III is carried out with at least 3 moles of chlorosulfonic acid per mole of compound of formula II in an inert solvent and in the temperature range from −10° to +80° C.

7. A process according to claim 6, wherein the reaction of the compound of formula II to give the compound of formula III is carried out with at least 5 moles of chlorosulfonic acid per mole of compound of formula II in the temperature range from −10° to +60° C. in methylene chloride, 1,2-dichloroethane or chloroform.

8. A process according to claim 1, wherein the reaction of the compound of formula III to give the compound of formula IV is carried out in an aqueous solution of ammonia.

9. A process according to claim 1, wherein the dehalogenation of the compound of formula IV to give the compound of formula V is carried out in tetrahydrofuran with hydrogen, under normal pressure at 20° to 25° C. and in the presence of a 5% palladium on carbon catalyst.

10. A process according to claim 1, wherein the hydrogenation of the compound of formula V to give the compound of formula I is carried out in tetrahydrofuran with hydrogen, in the temperature range from 30° to 50° C. under a pressure of 1 to 5 bar and in the presence of a 5% palladium on carbon catalyst.

11. A process according to claim 1, which comprises reacting a compound of formula II, wherein Hal is bromine or chlorine, with at least 5 moles of chlorosulfonic acid per mole of compound of formula II in the temperature range from −10° to +60° C., in methylene chloride, 1,2-dichloroethane or chloroform, treating the resultant sulfonyl chloride of formula III with an aqueous solution of ammonia, dehalogenating the sulfonamide of formula IV so obtained by catalytic hydrogenation in tetrahydrofuran with hydrogen, under normal pressure in the temperature range from 20° to 25° C. and in the presence of a 5% palladium on carbon catalyst, and hydrogenating the dehalogenated sulfonamide of formula V in the temperature range from 30° to 50° C. under a pressure of 1 to 5 bar in the presence of a 5% palladium on carbon catalyst.

* * * * *